Figure 1:
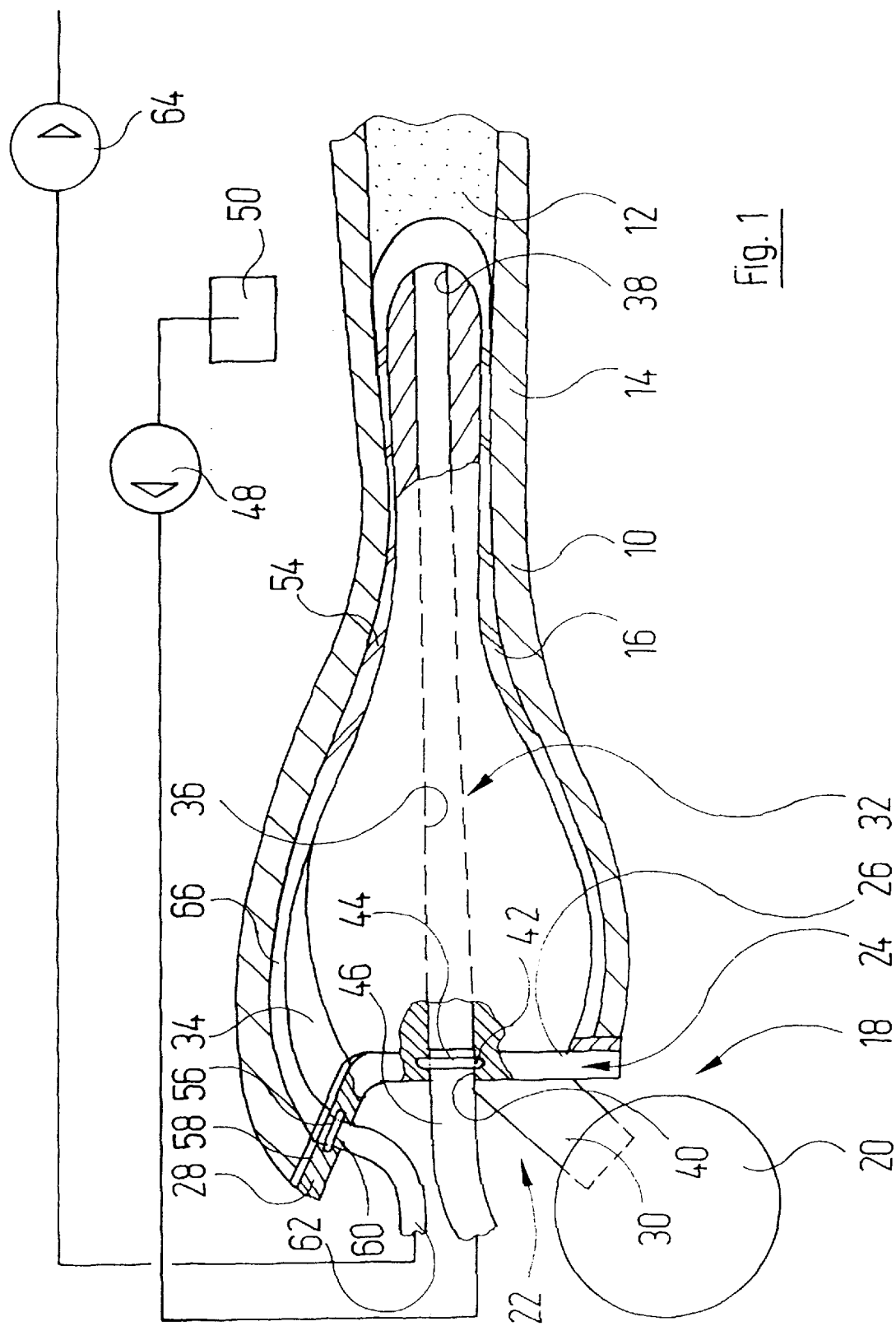

United States Patent
Copf

[19]

[11] Patent Number: 5,997,576
[45] Date of Patent: Dec. 7, 1999

[54] PROSTHESIS

[76] Inventor: Franz Copf, Marienstrasse 12, D-70178, Stuttgart, Germany

[21] Appl. No.: 09/154,549

[22] Filed: Sep. 16, 1998

[30] Foreign Application Priority Data

Sep. 16, 1997 [DE] Germany .......................... 197 40 690

[51] Int. Cl.⁶ .................. A61F 2/30; A61F 2/32
[52] U.S. Cl. .............................. 623/18; 623/22
[58] Field of Search ................. 623/16, 18, 20, 623/22

[56] References Cited

U.S. PATENT DOCUMENTS

| | | | |
|---|---|---|---|
| 4,399,814 | 8/1983 | Pratt, Jr. et al. | 128/92 |
| 4,562,598 | 1/1986 | Kranz | 623/18 |
| 4,888,022 | 12/1989 | Huebsch | 623/22 |
| 4,892,550 | 1/1990 | Huebsch | 623/22 |
| 5,782,917 | 7/1998 | Carn | 623/16 |
| 5,861,043 | 1/1999 | Carn | 623/16 |

FOREIGN PATENT DOCUMENTS

| | | | |
|---|---|---|---|
| 004228317 | 3/1994 | Germany | 623/18 |
| 004313201 | 11/1994 | Germany | 623/16 |
| 093011721 | 6/1993 | WIPO | 623/18 |

*Primary Examiner*—Paul J. Hirsch
*Assistant Examiner*—Michael B. Priddy

[57] ABSTRACT

A prosthesis which is to be incorporated with the aid of cement has a support plate (24), which projects beyond a shaft (32) on all sides. Constructed in the shaft is an axial supply duct (36) for cement and a suction aperture (56) is provided in a projecting lateral section (28) of the support plate (24). The distal boundary surface of the support plate (24) supports a plastically deformable sealing frame (52). In this manner, the space between the corticalis internal surface and the shaft external surface is closed in a sealing-tight manner and can be evacuated by a suction pump (64). As a result, the intermediate space between the corticalis and the shaft can be filled with cement in an inclusion-free manner.

18 Claims, 2 Drawing Sheets

PROSTHESIS

The invention relates to a prosthesis according to the preamble of claim 1.

In a prosthesis of this type according to the earlier application 196 13 081.6, it is even easily possible in the case of axially very long cavities to fill the intermediate space between the shaft external surface and the internal surface of the corticalis of the tubular bone cleared out in the end section with highly fluid cement, which fills the intermediate space between the corticalis internal surface and the shaft external surface and thus securely connects the prosthesis to the end of the bone.

Nevertheless, in some applications, in particular in the case of heavily bleeding cavities or also where cement having a somewhat higher viscosity is used, foreign fluid and/or air can become trapped. As a result, the strength of the connection between prosthesis and bone end is impaired.

It is therefore the object of the invention to further develop a prosthesis according to the preamble of claim 1 in such a manner that a cement layer which is free of inclusions is obtained even under the above-mentioned unfavourable operating conditions.

This object is attained according to the invention by a prosthesis having the features laid out in claim 1.

In a prosthesis according to the invention, the intermediate space between the corticalis internal surface and the shaft external surface is sealed relative to the environment by the circumferential sealing element of the support plate even when the corticalis at the end of the tubular bone is not resectioned precisely according to the contour of the support plate, which presents problems in practice. It is therefore possible to fully subject this intermediate space to an underpressure via the suction aperture provided in the support plate, and defined flow conditions are provided in this intermediate space for the cement which is released from the outlet aperture of the supply duct arrangement. As a result of the underpressure application, foreign fluids and air are also reliably drawn off, so that there are no inclusions in the cement layer.

The above-mentioned advantages are obtained with only a small amount of additional outlay: it is merely necessary to provide an additional opening in the support plate and to fit a sealing element onto the distal boundary surface of the support plate.

Advantageous further developments of the invention are laid out in the subclaims.

With the further development of the invention according to claim 2, the sealing between the support plate and edge of the corticalis is permanently obtained with a low application of force.

If the sealing element is made of highly viscous cement compound, as disclosed in claim 3, then following hardening of this cement compound an additional adhesive surface is obtained between the free edge of the corticalis and the distal boundary surface of the support plate, which is advantageous in respect of good force transmission between prosthesis and bone.

The further development of the invention according to claim 4 simplifies the handling of the prosthesis during an operation.

The further development of the invention according to claim 5 also allows for good sealing between the support plate and the edge of the corticalis irrespective of imprecisions in the resectioning of the corticalis.

In this respect, the further development of the invention according to claim 6 is advantageous if it is necessary to remove the sealing element following filling of the intermediate space between the corticalis internal surface and the shaft external surface. The sealing element can then easily be withdrawn between the edge of the corticalis and the distal boundary surface of the support plate. The space originally filled by the sealing element can also be filled with cement by secondary flow or re-pressing. In addition, the prosthesis can be struck in the distal direction, so that the distal boundary surface of the support plate is moved as close as possible to the edge of the corticalis.

The further development of the invention according to claim 7 is advantageous in respect of the withdrawal of the sealing element from the space between the corticalis and the distal boundary surface of the support plate.

The further development of the invention according to claim 8 is advantageous in respect of a preliminary axial securing of the prosthesis to the tubular bone, more particularly when working with an elastic sealing element, which compensates for the gap between the distal boundary surface of the support plate and the edge of the corticalis with varying local elastic deformation in the direction of its thickness.

With the further development of the invention according to claim 9, it is attained that the suction aperture is functional right up to the final part of the filling of the intermediate space between the shaft external surface and the corticalis internal surface.

The further developments of the invention according to claims 10 and 11 are advantageous in respect of easy manufacture and release of a sealing-tight connection between the connecting lines and support plate.

Figure 2:
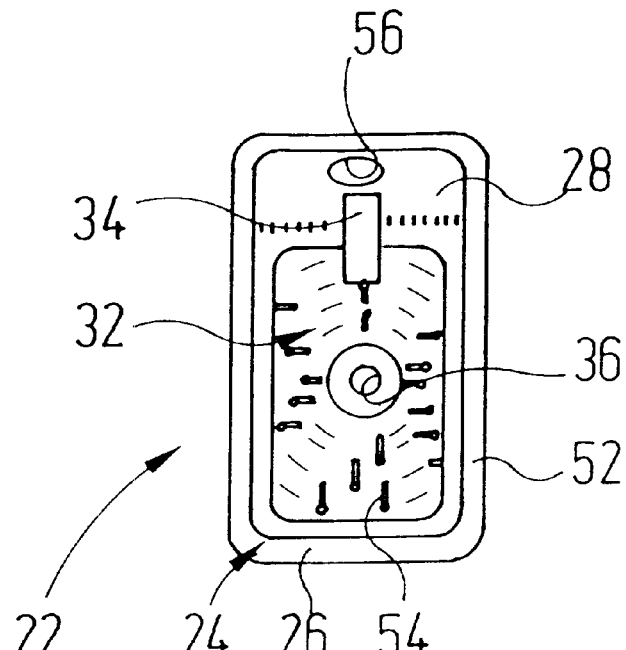
Figure 3:
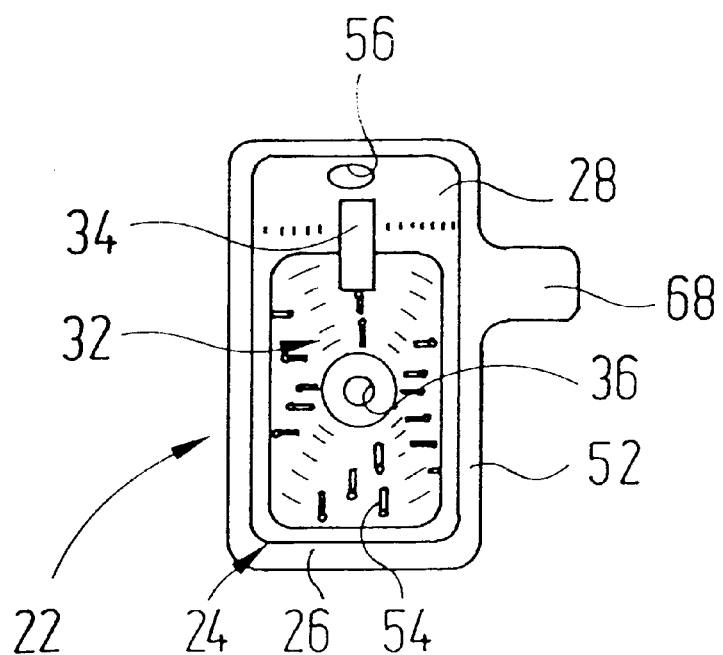

The invention will be explained in further detail in the following with the aid of embodiments with reference to the drawings, in which:

FIG. 1: is a longitudinal section through the end of a thigh bone with a thigh prosthesis introduced therein, shown under operating conditions;

FIG. 2: is an axial view of the distal end of a shaft of the prosthesis shown in FIG. 1; and FIG. 3: is a view similar to FIG. 2, in which a modified prosthesis is shown.

In FIG. 1, the reference 10 indicates the upper end section of a femur. The greater trochanter supporting the condyle is resectioned, the resectioning surface lying substantially perpendicular to the axis of the thigh bone and rising towards the proximal end in an upper section in FIG. 1.

Proximal corresponds to the left in FIG. 1, distal to the right in FIG. 1. In the following description, the direction references lateral and medial as well as dorsal and ventral are also used. Lateral means upwards in FIG. 1, medial downwards in FIG. 1. Dorsal in FIG. 1 means perpendicular to the plane of the drawing in a rearward direction, ventral in FIG. 1 means perpendicular to the plane of the drawing in a forward direction.

The spongiosa, which is still shown in the right-hand part of the femur at 12, is removed from the resectioned end of the femur 10, so that the external corticalis 14 defines a cavity 16.

A prosthesis, designated in its entirety by the reference 18, is inserted into the cavity 16. The prosthesis comprises a condyle 20, which is made of ceramic material and is polished on its surface, and a prosthesis element designated in its entirety by the reference 22.

The latter comprises an angled support plate 24 with a main section 26 lying perpendicular to the femur axis and a lateral section 28 tilted in the proximal direction. The resectioning of the bone end has been carried out according to the contour of the support plate 24. The peripheral contour of the support plate 24 corresponds to the peripheral contour of the corticalis 14 at the resectioning surface.

The proximal boundary surface of the support plate 24 supports a moulded-on support post 30, to which the condyle 20 is secured.

The distal boundary surface of the support plate 24 supports a shaft 32, whose outer cylindrical surface follows the internal surface of the corticalis with a small clearance. As can be seen from the drawing, the transverse cross section of the shaft 32 decreases towards its distal end.

In practice, the transverse cross section of the shaft 32 can correspond approximately to a rectangle with rounded corners. In the region of the remaining part of the greater trochanter, a rib 34 imitating the course of the trochanter is fitted onto the outer surface of the shaft 32.

Extending through the support plate 24 and the shaft 32 is a supply duct 36, which intersects the end face of the shaft 32 where it presents an outlet aperture 38. The supply duct 36 opens proximally into the support plate 24, where it presents a supply aperture 40. Cut into the supply aperture 40 is an annular groove 42, which can accommodate an annular bead 44 with elastic compression, which is provided in the end section of a supply tube 46. The latter leads to the delivery side of a cement feed pump 48, which draws from a cement supply receptacle 50.

As shown in particular in FIG. 2, the support plate 24 projects beyond the shaft 32 on all sides. Its edge is flush with the external surface of the corticalis 14, as already illustrated. In the peripheral region lying opposite the free end face of the corticalis 14 formed by resectioning, the support plate 24 supports a circumferential sealing frame 52. In the embodiment shown in FIGS. 1 and 2, this is formed by a layer of highly viscous cement material. This may be the same cement material which is used to connect the shaft 32 to the internal surface of the corticalis 14, additional fillers being added to the sealing frame material and/or the composition of the cement being modified in such a manner that the hardening occurs more slowly. In this case, the highly viscous cement material can also be partially hardened or pre-dried. In practice, the thickness of the sealing frame 52 can be approximately 1 to 5 mm, preferably 2 to 4 mm. In this manner, the sealing frame 52 can compensate the contour deviations between the exposed end face of the corticalis and the distal boundary surface of the support plate 24, which are unavoidable during resectioning. When the prosthesis 18 is pushed into the cavity 16, excess material of the sealing frame 52 is displaced.

In order to secure the position obtained by pushing the prosthesis into the cavity, the outer curved surface of the shaft 32 comprises short wire elements 54, which are inclined towards the distal end and whose length can be 5 mm in practice. The angle of pitch of the wire elements 54 relative to the shaft axis can be approximately 60° in practice. By elastically bending the wire elements in the direction of the distal end, the ends of the wire elements 54 can adapt to the actual contour of the corticalis internal surface. The end faces of the wire elements hook onto rough edges on the corticalis internal surface or work themselves into residual layers of spongiosa supported by the corticalis internal surface. The wire elements 54 thus form barbs acting in the distal direction.

A suction aperture 56 is provided in the lateral section 28 of the support plate. Provided in the suction aperture 56 is a circumferential annular groove 58, which cooperates with a matching, elastically deformable annular bead 60 at the end of a section tube 62. The latter leads to the suction side of a suction pump 64.

The prosthesis described above is implanted as follows:

After forming the cavity 16, the prosthesis 18 is introduced into the cavity 16 in the distal direction, the sealing frame 52 supported by the boundary surface of the support plate 24 being plastically deformed during the last part of the movement to match the actual contour of the corticalis edge. At the end of the introduction procedure, the support plate 24 sits with a plurality of partial regions directly on the regions of the edge of the corticalis lying in front of the ideal resectioning surface. The intermediate spaces remaining between the rest of the distal boundary surface of the support plate 24 and the end face of the corticalis 14 are sealed by the sealing frame 52. During the introduction into the cavity 16, the wire elements 54 were additionally bent and hooked onto the corticalis internal surface. In this manner, the position of the prosthesis 18 in the bone end is provisionally fixed. The supply tube 46 and the suction tube 52 are then connected to the supply aperture 40 and the suction aperture 56 respectively. The space 66 lying between the shaft external surface and the corticalis internal surface is then evacuated by the suction pump 64. During this process, fluid which has collected in the cavity 16 is drawn off. The cement supply via the supply tube 46 is then started and the cavity 16 is supplied with highly fluid cement from the distal end via the supply tube 46. The cement flowing out of the outlet aperture 38 firstly flows downwards into the cavity 16 under the force of gravity and fills the cavity from the bottom upwards. This filling of the cavity is effected with further continuous evacuation, so that quantities of fluid lying in front of the cement surface are reliably extracted and air is prevented from being trapped. At the end of the filling procedure, fluid cement then flows into the suction tube 62. At this point in time, the filling can be ended.

Following hardening of the cement, the supply tube 46 and the suction tube 42 can be directly removed at the proximal boundary surface of the support plate.

In the modified embodiment according to FIG. 3, the sealing frame 52 is manufactured from an elastomer material. It is adhered to the support plate by means of a biocompatible adhesive layer which can be easily broken open or by pinning onto thin and short distal needles of the support plate and can therefore be handled integrally with the prosthesis.

Provided at the edge of the sealing frame 52 is a gripping flange 68, onto which, following the filling of the space 66, the sealing frame 52 can be drawn in a radially outward direction and over the edge of the support plate 24 in the proximal direction. After cutting, the sealing frame 52 can then be removed.

As a modification to the above embodiments, it is also possible to use plastically deformable ceramic foam materials, plastically deformable metals or metal foams or plastically deformable plastics material foam materials or corresponding plastically deformable sinter materials made of the above-mentioned substances as material for the sealing frame.

I claim:

1. A prosthesis with an elongated shaft, which can be introduced into a cavity cleared in an end section of a tubular bone and comprises a supply duct arrangement, which comprises at least one outlet aperture opening onto at least one of the curved outer surface and the end face of the shaft, and a supply aperture opening onto a support plate, the support plate projecting at least in a partial region of its peripheral section beyond the shaft, wherein a suction aperture penetrating the support plate is provided in the projecting region of the peripheral section and the distal boundary surface of the support plate supports a circumferential sealing element.

2. A prosthesis as claimed in claim 1, wherein the sealing element (52) is plastically deformable.

3. A prosthesis as claimed in claim 2, wherein the sealing element (52) comprises a highly viscous cement compound.

4. A prosthesis as claimed in claim 3, wherein the cement compound is pre-dried or pre-hardened.

5. A prosthesis as claimed in claim 2, wherein the sealing element is made of a foam material.

6. A prosthesis as claimed in claim 1, wherein the sealing element (52) is manufactured from tough material which can be subjected to tensile loading.

7. A prosthesis as claimed in claim 6, wherein the sealing element (52) comprises a radially outwardly projecting gripping flange (68).

8. A prosthesis as claimed in claim 1, wherein the external surface of the shaft comprises a plurality of retaining elements angled towards a proximal end of the shaft.

9. A prosthesis as claimed in claim 1, wherein the suction aperture is provided in the uppermost region of the support plate under operating conditions.

10. A prosthesis as claimed in claim 1, wherein at least one of a supply line for cement and a suction line comprise locking means, which cooperate with the support plate.

11. A prosthesis as claimed in claim 10, wherein the locking means have the form of an elastic annular bead (44, 60), which cooperates with an annular groove (42, 58) of the supply aperture (40) or of the suction aperture (56).

12. A prosthesis as claimed in claim 2, wherein the sealing element is made of a sinter material.

13. A prosthesis as claimed in claim 5, wherein the foam material is a tissue-compatible inorganic material.

14. A prosthesis as claimed in claim 12, wherein the sinter material is a tissue-compatible inorganic material.

15. A prosthesis as claimed in claim 13, wherein the tissue-compatible inorganic material is a polyethylene foam.

16. A prosthesis as claimed in claim 14, wherein the tissue-compatible inorganic material is a polyethylene foam.

17. A prosthesis as claimed in claim 6, wherein the sealing element is an elastomer.

18. A prosthesis as claimed in claim 8, wherein the plurality of retaining elements are in the form of wire elements.

* * * * *